United States Patent [19]

Rohr et al.

[11] Patent Number: 4,472,247
[45] Date of Patent: Sep. 18, 1984

[54] METHOD FOR MEASURING THE OXYGEN CONCENTRATION IN GAS MIXTURES

[75] Inventors: Franz-Josef Rohr, Abtsteinach; Henner Meinhold, Sandhausen, both of Fed. Rep. of Germany

[73] Assignee: Brown, Boveri & Cie AG, Manheim-Käfertal, Fed. Rep. of Germany

[21] Appl. No.: 562,863

[22] Filed: Dec. 19, 1983

[30] Foreign Application Priority Data

Dec. 24, 1982 [DE] Fed. Rep. of Germany ....... 3247920

[51] Int. Cl.$^3$ .......................................... G01N 27/58
[52] U.S. Cl. .................................. 204/1 T; 204/406; 204/425
[58] Field of Search ................ 204/406, 410, 425, 1 S; 123/489; 60/276

[56] References Cited

U.S. PATENT DOCUMENTS 4,355,618 10/1982 Müller et al. ................. 123/489

FOREIGN PATENT DOCUMENTS 2083629 3/1982 United Kingdom ............... 204/406

Primary Examiner—G. L. Kaplan
Attorney, Agent, or Firm—Herbert L. Lerner; Laurence A. Greenberg

[57] ABSTRACT

Method for measuring the free oxygen concentration in gas mixtures, especially combustion gases, with an electrochemical measuring device which comprises an oxygen ion-conducting solid electrolyte and two electrodes to which the supply voltage $U_s$ is fed. The supply voltage $U_s$ is formed from the sum of at least two voltage components $U_a$ and $U_v$. The first voltage component $U_a$ is kept at a constant predeterminable value which is required for ionizing the free oxygen. The second voltage component $U_v$ is kept variable and its respective value is determined as a function of the magnitude of the probe current $I_s$ flowing between the electrodes.

15 Claims, 4 Drawing Figures

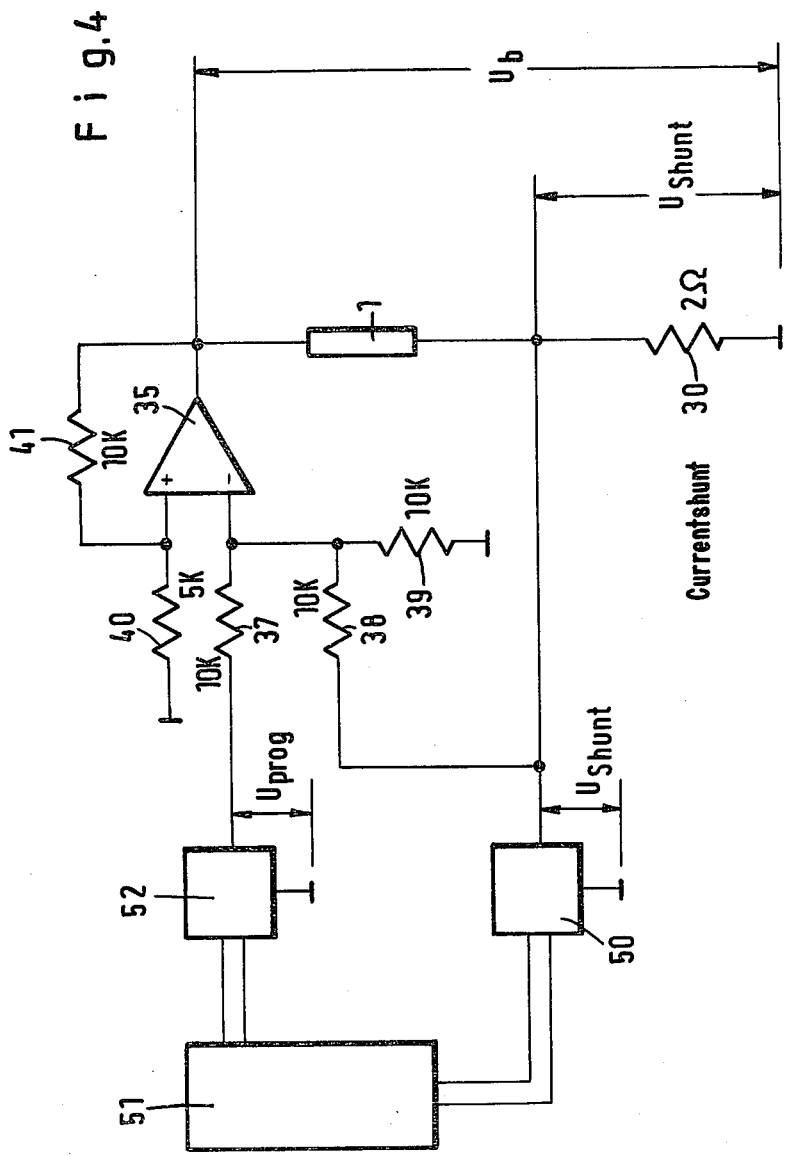

METHOD FOR MEASURING THE OXYGEN CONCENTRATION IN GAS MIXTURES

BACKGROUND OF THE INVENTION

1. Field of the Invention

The invention relates to a method for measuring the oxygen content in gas mixtures, especially combustion gases, with an electrochemical measuring device which has an oxygen ion-conducting solid electrolyte and two electrodes to which a supply voltage is fed, as well as a circuit for carrying out the method.

2. Description of the Prior Art

Such a method is used preferably for determining the free oxygen content in exhaust gases of combustion plants burning oil, gas and coal.

In determining these oxygen measurements, a measuring device with a measuring probe which has at least one solid electrolyte of the zirconium oxide type and two electrodes, to which a d-c voltage is applied is preferably used. A measuring device of this type is disclosed in German Published Non-Prosecuted Application DE-OS No. 30 38 429, the first electrode of which, serving as the cathode, is acted on by the gas stream to be measured. Thereby, the free oxygen content is extracted electrolytically from the gas stream and is transported in the form of oxygen ions through the solid electrolyte to the second electrode and recombined there to form oxygen molecules. A current signal between the electrodes is formed due to the oxygen ions traveling through the solid electrolyte. This current signal is independent of the temperature if the operating temperature in this measuring method is kept above a critical value of 650° C. During the measurement, the quantity of the sample gas must be kept constant. This can be achieved in the simplest manner by means of a critical nozzle. If these conditions are observed, the direct proportionality between the probe current and the oxygen concentration is maintained.

A disadvantage of this measuring method is that, depending on the magnitude of the probe voltage applied, in addition to the molecular oxygen which is present, chemically bound oxygen is also liberated by electrolytic dissociation of oxygen-containing compounds such as water, carbon dioxide and nitrogen oxides of the gas sample. This electrolytic dissociation of oxygen-containing compounds causes a falsification of the measurement result proper, and a higher oxygen content is indicated in the gas to be measured than is actually present.

SUMMARY OF THE INVENTION

An object of the invention is to provide a method for measuring the oxygen concentration in gas mixtures with a measuring device delivering a current signal as the measurement variable, in which the electrolytic dissociation of oxygen-containing compounds in the gas mixture to liberate free oxygen is prevented and thereby a more exact determination of the free oxygen content in a gas can be made and the speed of response of the measuring device in the event of a change in the oxygen concentration is increased.

With the foregoing and other objects in view, there is provided in accordance with the invention a method for measuring the free oxygen concentration in a gas mixture which contains oxygen-containing compounds with an electrochemical measuring device which comprises an oxygen ion-conduction solid electrolyte and two electrodes to which a supply voltage $U_s$ is fed, passing the gas mixture in contact with one of said two electrodes causing the flow of free oxygen in the gas mixture in the form of oxygen ions through the solid electrolyte with probe current $I_s$ flowing between the electrodes, the improvement comprising preventing electrolytic dissociation of the oxygen-containing compounds with formation of free oxygen therefrom of forming the supply voltage $U_s$ from the sum of at least two voltage components $U_a$ and $U_v$, keeping the first voltage $U_a$ at a constant predeterminable value which is required for ionizing the free oxygen, and keeping the second voltage component $U_v$ variable and determining its respective value as a function of the magnitude of the probe current $I_s$ flowing between the electrodes.

In accordance with the invention, there is provided a circuit wherein the voltage output of the measuring device is connected to a current shunt and into this electrical connection, the positive input of a first voltage amplifier is connected via a potentiometer and a resistor time delay stage; wherein the output of the first voltage amplifier is connected to the negative input of a second voltage amplifier which is additionally connected to the constant voltage $U_a$, to the voltage output of the measuring device as well as to ground via an ohmic resistor; and wherein the output of the second voltage amplifier is connected as the d-c voltage source to the measuring device.

There is provided in accordance with the invention a circuit wherein the voltage output of the measuring device is connected to a current shunt and the input of an analog-to-digital converter is inserted into this electrical connection, the output of which is connected to a microprocessor which is followed by a digital-to-analog converter; wherein the output of the digital-to-analog converter is connected via an ohmic resistor to the negative input of a voltage amplifier, the output of which serves as the d-c voltage source and is connected to the measuring device; wherein the negative input of the voltage amplifier is additionally connected via an ohmic resistor to the voltage output of the measuring device and to ground; and wherein the positive input of the voltage amplifier is connected via an ohmic resistor to ground and another ohmic resistor to the output of the voltage amplifier.

Other features which are considered as characteristic for the invention are set forth in the appended claims.

Although the invention is illustrated and described herein as embodied in a method and circuit for measuring the oxygen concentration in gas mixtures, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings, in which:

FIG. 4 is a variant of the circuit shown in FIG. 3.

DETAILED DESCRIPTION OF THE INVENTION

Figure 1:
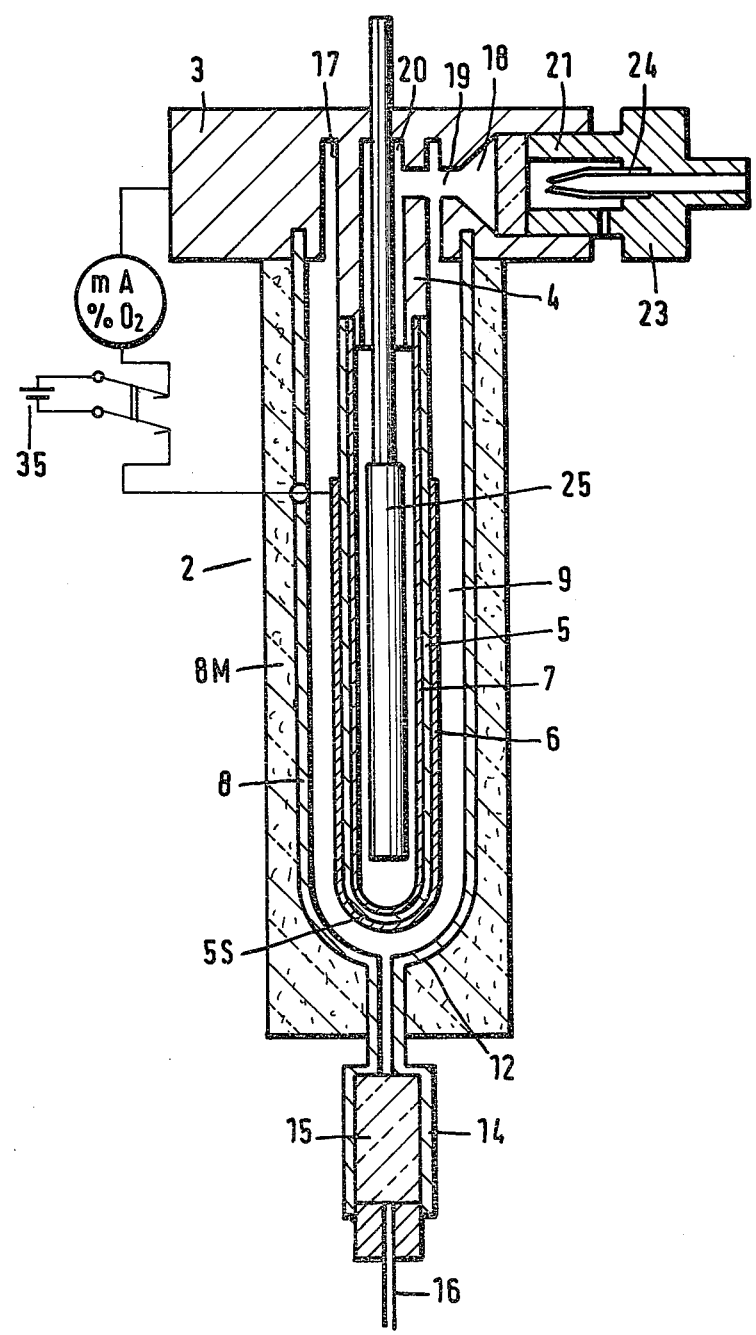
FIG. 1 shows the basic design of a measuring device with a current signal as the measuring variable, FIG. 2 graphically shows the current/voltage characteristic of the measuring device shown in FIG. 1.

The invention relates to a method for measuring the free oxygen concentration in gas mixtures, with an electrochemical measuring device which is provided with a solid electrolyte, which has two electrodes which are connected to a d-c voltage source. According to the invention, a supply voltage $U_s$ which consists of two voltage components $U_a$ and $U_v$ is fed to the measuring device. The first voltage component $U_a$ has a constant predeterminable value which is maximally 600 mV. The second voltage component $U_v$ has a variable value which is determined and regulated as a function of the magnitude of the probe current $I_s$ flowing between the electrodes of the measuring device.

The d-c voltage source for the measuring device serves as a voltage amplifier. A constant voltage $U_a$ is fed to the negative input of the voltage amplifier. In addition, this input is connected to the output of a further voltage amplifier, the positive input of which is connected via a time delay stage and a potentiometer to the voltage output of the measuring device. A current shunt is connected as a bypass parallel to the potentiometer.

According to the invention, the probe voltage which is applied to the electrodes of the measuring device for carrying out the measurement, is matched to the respective magnitude of the instantaneous probe current $I_s$. It is possible thereby to avoid the overvoltage at the electrodes which caused the electrolysis of nitrogen oxide, carbon dioxide and water and the measurement error connected therewith. If the concentration of free oxygen within a quantity of gas to be tested is low, deviations which may be up to 1% oxygen, are eliminated completely by the method according to the invention.

To make possible an optimum measurement of the free oxygen concentration in the amount of gas to be tested, a voltage $U_s$ is applied to the electrodes of the measuring device, $U_s$ consists of two voltage components $U_a$ and $U_v$. $U_a$ stands for a constant base voltage which is preferably chosen in an order of magnitude of 100 to 600 mV. This base voltage $U_a$ is chosen so that an electrolytic dissociation of nitrogen oxide, carbon dioxide and water will not occur with the lowest free oxygen concentrations in the gas to be tested. $U_v$ is a variable voltage which is proportional to the current flowing between the electrodes of the measuring device. This voltage is determined substantially by multiplication of the probe current $I_s$ by the slope $\Delta U/\Delta I$ of the current-voltage characteristic of the measuring probe. The voltage of the measuring device $U_s$ must be limited to an upper limit, preferably to $U_g \leq 1.4$ V in order to prevent electrolytic dissociation of the solid electrolyte made of zirconium oxide.

In the method according to the invention, the supply voltage $U_s$ of the measuring device is thereby varied automatically between a lower voltage value which corresponds to the constant value of the voltage $U_a$ and an upper voltage limit proportional to the current.

The circuit for implementing the method according to the invention is designed so that the proportionality factor determined from the slope $\Delta U/\Delta I$ of the current-voltage characteristic of the measuring device, by which the probe current is multiplied for determining the variable voltage $U_v$, can be set at the potentiometer of the circuit after its theoretical determination from the current-voltage curve of the measuring device. With the circuit according to the invention, the voltages $U_s$ which are to be fed to the measuring device can be set to a maximum value which is approximately 1400 mV. The minimum value of the supply voltage $U_s$ is limited to $U_a \geq 200$ mV. According to the invention, the voltage output of the measuring device is connected to a current shunt. Into this electrical connection is connected the positive input of a first voltage amplifier via a potentiometer and a time delay stage. The output of this voltage amplifier is connected to the negative input of a second voltage amplifier. The negative input of the second voltage amplifier is additionally connected to the voltage output of the measuring device as well as to ground via an ohmic resistor. The output of this second voltage amplifier serves as a d-c voltage source for the measuring device. In the circuit according to the invention, the second terminal of the current shunt and of the potentiometer is connected to ground. The tap of the potentiometer is connected to the resistor of the time delay stage. The negative input of the voltage amplifier is in connection with the output thereof. To the negative input of the second voltage amplifier are fed, the output signal of the measuring device and the output signal of the first voltage amplifier as well as the constant voltage $U_a$ via an ohmic resistance each.

In a simplified embodiment of this circuit, the voltage output of the measuring device is connected to a current shunt. Into this electrical connection is connected the input of an analog-to-digital converter, the output of which is connected to a microprocessor. The latter is followed by a digital-to-analog converter, the output of which is in connection with the negative input of a voltage amplifier. The voltage amplifier serves as the d-c voltage source and is connected to the measuring device. The negative input of this voltage amplifier is additionally connected via an ohmic resistor to the voltage output of the measuring device and to ground. The positive input of this voltage amplifier is connected via an ohmic resistance each, for one, to ground and secondly, to the output of the voltage amplifier.

The invention will be explained in the following with the aid of drawings.

The electrochemical measuring device shown in FIG. 1 comprises a tubular measuring cell 2 with a flange of metal 3 terminating the measuring cell 2. A circular projection 4 protrudes from one base surface of the flange 3. A solid electrolyte tube 5 is fastened to the free end of projection 4. The outside of the tube 5 is the first electrode 6 which covers, as seen from the end 5S of the solid electrolyte tube 5, about two-thirds of the length of the solid electrolyte tube. On the inside of the solid electrolyte tube 5, the second electrode 7 extends from the end 5S to the fastening point of the solid electrolyte tube 5 at the projection 4 and is in electrically conducting contact with the projection 4. The two electrodes 6 and 7 consist of a porous electron-conducting layer, through which the oxygen can diffuse unhindered. The solid electrolyte tube 5 is surrounded by a cladding tube 8, which is spaced from tube 5 to leave a continuous empty space 9 between the first electrode 6 and the cladding tube 8. The inside width of this empty space 9 is about 0.3 to 2 mm in the radial direction and preferably about 0.5 mm. The cladding tube 8 is inserted gas-tight into an annular recess of the flange 3 and fastened there. The space 9 between the cladding tube 8 and the solid electrolyte is part of the measuring gas canal. At the lower end 12 of the cladding tube 8, a narrow gas feeding tube is provided which, in an enlarged part 14, has a gas filter 15 which may consist, for instance, of glass wool or a porous ceramic body. The enlarged part 14 is provided with a capillary tube 16, through which the gas to be measured is fed-in. The cladding tube 8, is surrounded by an insulating jactet 8M which extends up to the flange 3. The annular projection 4 arranged at the flange 3 is surrounded by a concentric annular gap 17 which extends in the flange 3. Annular gap 17 opens into the space 9 and is connected to a space 18 of circular cross section which extends transversely to the longitudinal axis of the measuring cell 2. The connecting hole 19 which extends perpendicularly to the longitudinal axis of the measuring cell 2 is continued in the direction toward the longitudinal axis, so that the interior 20 of the projection 4 which forms a unit with the interior of the solid electrolyte 5, is also connected to the space 18. The latter is preferably formed as a drill hole and has a thread, into which an insert 21 is screwed by means of a head 23 provided at the insert. The portion of the insert 21 protruding into the base body 3 comprises a disc-shaped filter.

A nozzle 24 is installed in the head 23 of the insert 21, which nozzle serves to hold the flow of gas constant. A heater 25 is installed in the interior of the solid elecrolyte tube 5, to keep the measuring cell 2 at the required operating temperature. In order that the necessary supply voltage can be applied to the two electrodes 6 and 7, an electrical line (not shown here) is brought from the first electrode 6 radially outward. The second electrode 7 is connected in an electrically conducting manner to the flange 3 via the centering projection and via a further projection of the flange 3. The supply voltage $U_s$ is applied to the flange 3 and the above-mentioned electrical line.

Figure 2:
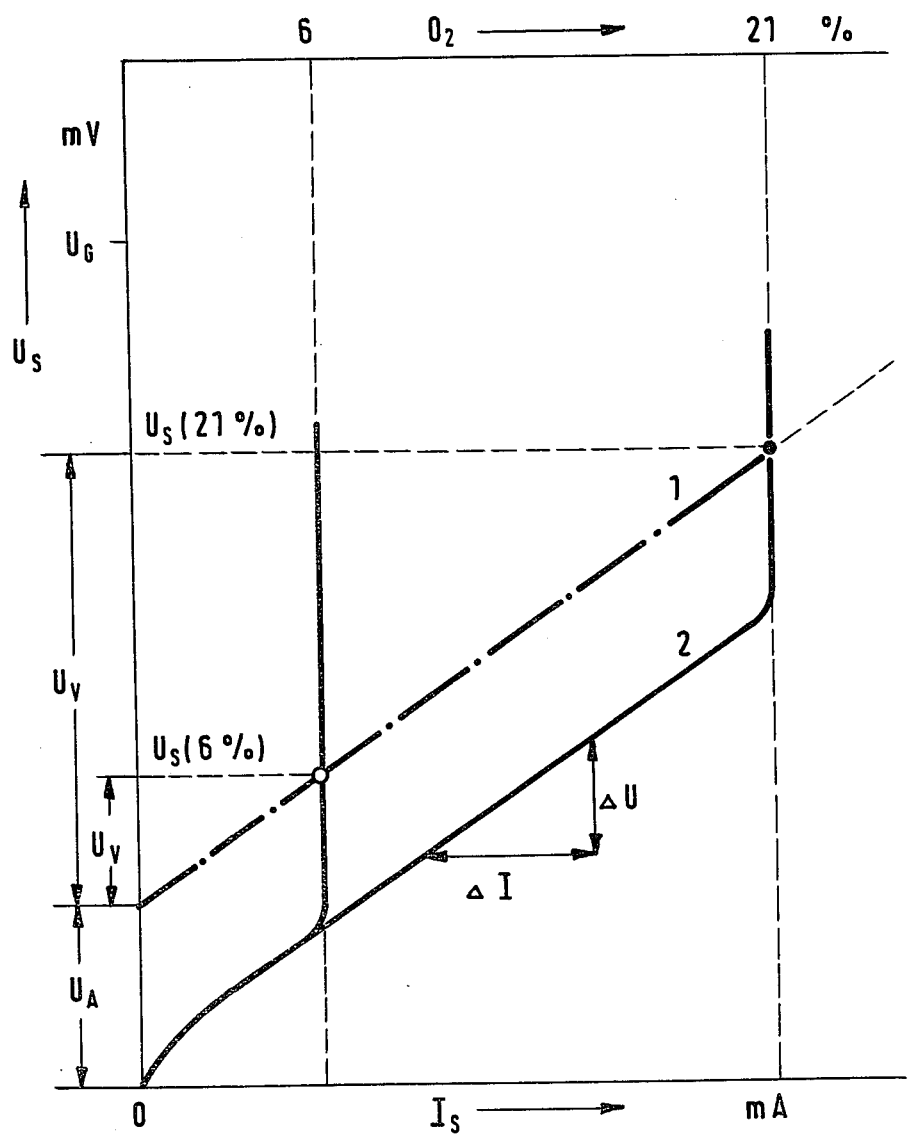
Figure 3:
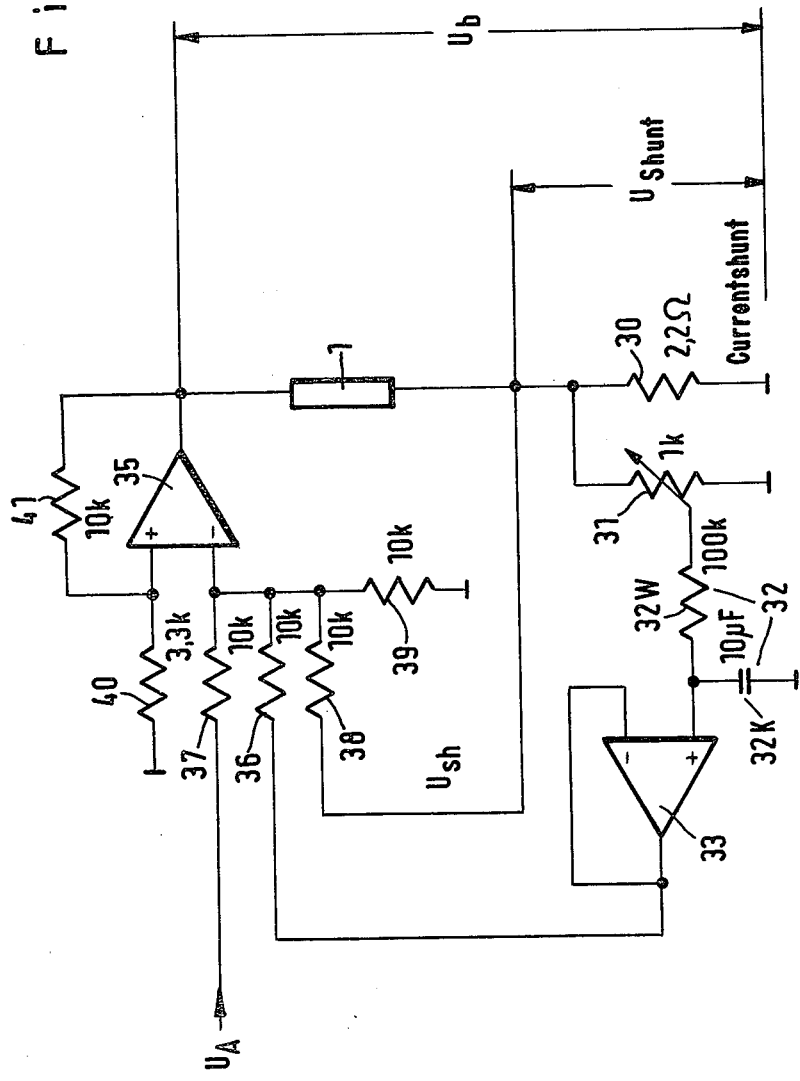
FIG. 3 shows a circuit for forming the voltage $U_s$ for the measuring device according to FIG. 1.

In FIG. 2, the current-voltage characteristic of this measuring device is shown. The slope of this characteristic is required for determining the voltage $U_s$, the magnitude of which is determined, according to the invention, as a function of the probe current $I_s$ which flows between the electrodes 6 and 7 of the measuring device, and the magnitude of which in turn depends on the quantity of free oxygen within the gas to be measured. In order that the supply voltage $U_s$ required according to the method of the invention can be fed to the measuring device 1, the circuit shown in FIG. 3 is required. The supply voltage $U_s$ to be fed to the measuring device 1 is formed by two voltage components. The first voltage component $U_a$ is an adjustable constant voltage which has a value between 100 and 600 mV. The second voltage component is kept variable. Its magnitude is determined, in particular, by the magnitude of the current signal at the measuring device 1. For determining it, the probe current $I_s$ is multiplied by the slope of the current-voltage characteristic, $\alpha = \Delta U/\Delta I$, of the measuring device 1. This multiplication factor $\alpha$ is a magnitude specific to the measuring device and is determined from the characteristic shown in FIG. 2.

According to the invention, a voltage $U_s$ which is determined by the following equation, is fed to the measuring device 1 and in particular, to its two electrodes:

$$U_s = U_a + \alpha I_s$$

$$\alpha = \Delta U/\Delta I$$

In the drawing shown in FIG. 3, the measuring device 1 is only indicated schematically. The current output signal $I_s$ or the voltage drop present at the measuring device 1 is fed via a current shunt 30 and an adjustable potentiometer 31 as well as a time delay stage 32 to the positive input of a first voltage amplifier 33. The current shunt 30 is formed by an ohmic resistance, the input of which is connected to the measuring device 1 in an electrically conducting manner. The output of this ohmic resistor is connected to ground. The input of the potentiometer 31 is connected between the output of the measuring device 1 and the input of the ohmic resistor 30. The output of the potentiometer 31 is likewise connected to ground. Its tap is connected to the input of the resistor 32W of 100 kohm which forms part of the delay stage 32. The output of this resistor 32W is connected to the positive input of the voltage amplifier 33. The first terminal of the capacitor 32K with a capacitance of 10 uF, which is part of the time delay stage is connected into the electric connection of this amplifier 33 and the ohmic resistor 32W, and the second capacitor electrode is connected to ground. The negative input of the voltage amplifier 33 is connected to the output of the amplifier 33. The voltage present at the output of the amplifier 33 is fed to the negative input of a second voltage amplifier 35 via an ohmic resistor 36. The constant voltage $U_a$ is fed to the negative input of the voltage amplifier 35 via an ohmic resistor 37 of the same resistance. In the embodiment example described here, this voltage $U_a$ has a value of 300 mV. Furthermore, the voltage drop present at the measuring device is fed to the negative input of the voltage amplifier 35 via an ohmic resistor 38 which has the same size as the ohmic resistors 36 and 37. The negative input of the voltage amplifier 35 is additionally connected to ground via a further ohmic resistor 39. The resistors 36, 37 and 38 all have a resistance of 10 kohm. The positive input of the voltage amplifier 35 is connected to ground via a 3.3 kohm resistor 40. It is further connected to the output of the voltage amplifier 35 via a 10 kohm resistor 41. The output of the voltage amplifier 35 is connected to the voltage terminals of the measuring device 1 in an electrically conducting manner.

As may be seen from FIG. 3, the voltages $U_b$ and $U_{shunt}$ are applied to the circuit. The voltage to be fed to the measuring device 1 (that from the voltage amplifier 35) can be calculated in accordance with the following equation:

$$U_b - U_{shunt} = U_a + \alpha I_{verz}$$

Therewith, one obtains for the supply voltage $$U_s = U_a + \alpha I_{verz}$$

The current $I_{verz}$ corresponds to the delayer probe current.

A simplified embodiment of the circuit described above is shown in FIG. 4. The voltage output of the measuring device 1 is again connected to a current shunt 30, the second terminal of which is tied to ground. Into this electrical connection is inserted the input of an analog-to-digital converter 50. The outputs of this converter 50 are connected to a microprocessor 51. The latter is followed by a digital-to-analog converter 52. The output of the converter 52 is connected via an ohmic resistor 37 to the negative input of a voltage amplifier 35. This negative input is additionally connected via an ohmic resistor 38 and 39, respectively, to ground and to the voltage output of the measuring device. The voltage amplifier 35 serves as the d-c voltage source and is connected to the measuring device and in particular, to its electrodes. The positive input of this voltage amplifier is connected to ground via an ohmic resistor 40 and to the output of the voltage amplifier 35.

The voltage drop which is present at the measuring device 1 is fed continuously to the microprocessor via the analog-to-digital converter 50. The microprocessor computes therefrom the supply voltage $U_s$ required for the measuring device and delivers a corresponding signal to the digital-to-analog converter following it. The latter feeds the voltage $U_{prog}$ to the voltage amplifier 35. This voltage corresponds to the supply voltage $U_s$ which is to be fed to the measuring device from the output of the voltage amplifier 35.

The foregoing is a description corresponding, in substance, to German application No. P 32 47 920.4, dated Dec. 24, 1982, international priority of which is being claimed for the instant application, and which is hereby made part of this application. Any material discrepancies between the foregoing specification and the specification of the aforementioned corresponding German application are to be resolved in favor of the latter.

We claim:

1. Method for measuring the free oxygen concentration in a gas mixture which contains oxygen-containing compounds with an electrochemical measuring device which comprises an oxygen ion-conduction solid electrolyte and two electrodes to which a supply voltage $U_s$ is fed, passing the gas mixture in contact with one of said two electrodes causing the flow of free oxygen in the gas mixture in the form of oxygen ions through the solid electrolyte with probe current $I_s$ flowing between the electrodes, the improvement comprising preventing electrolytic dissociation of the oxygen-containing compounds with formation of free oxygen therefrom by forming the supply voltage $U_s$ from the sum of at least two voltage components $U_a$ and $U_v$, keeping the first voltage $U_a$ at a constant predeterminable value which is required for ionizing the free oxygen, and keeping the second voltage component $U_v$ variable and determining its respective value as a function of the magnitude of the probe current $I_s$ flowing between the electrodes.

2. Method according to claim 1, wherein the gas mixtures are combustion gases.

3. Method acording to claim 2, wherein the supply voltage $U_s$ of the measuring device is limited to a maximum value of 1.4 V.

4. Method according to the claim 2, wherein the voltage $U_a$ is set to a value between 0.1 and 0.6 V.

5. Method according to claim 1, wherein the second voltage component $U_v$ is formed by multiplying the probe current $I_s$ by the quantity $\Delta U/\Delta I$, where this multiplication factor $\alpha$ corresponds to the slope of the current-voltage characteristic of the measuring device.

6. Method according to claim 1, wherein the supply voltage $U_s$ of the measuring device is limited to a maximum value of 1.4 V.

7. Method according to claim 1, wherein the voltage $U_a$ is set to a value between 0.1 and 0.6 V.

8. Method according to claim 1, wherein the two electrodes are connected to a d-c voltage source, including a circuit wherein the voltage output of the measuring device is connected to a current shunt and into this electrical connection, the positive input of a first voltage amplifier is connected via a potentiometer and a resistor time delay stage; wherein the output of the first voltage amplifier is connected to the negative input of a second voltage amplifier which is additionally connected to the constant voltage $U_a$, to the voltage output of the measuring device as well as to ground via an ohmic resistor; and wherein the output of the second voltage amplifier is connected as the d-c voltage source to the measuring device.

9. Method according to claim 8, wherein the second terminal of the current shunt and the potentiometer are connected to ground.

10. Method according to claim 9, wherein the tap of the potentiometer is connected to the resistor of the time delay stage.

11. Method according to claim 8, wherein the tap of the potentiometer is connected to the resistor of the time delay stage.

12. Method according to claim 8, wherein the negative input of the first voltage amplifier is connected to the output of the same.

13. Method according to claim 12, wherein the output signal of the measuring device and of the first voltage amplifier and the constant voltage $U_a$ are each fed via an ohmic resistor to the negative input of the second voltage amplifier.

14. Method according to claim 8, wherein the output signal of the measuring device and of the first voltage amplifier and the constant voltage $U_a$ are each fed via an ohmic resistor to the negative input of the second voltage amplifier.

15. Method according to claim 1, wherein the two electrodes are connected to a d-c voltage source, including a circuit wherein the voltage output of the measuring device is connected to a current shunt and the input of an analog-to-digital converter is inserted into this electrical connection, the output of which is connected to a microprocessor which is followed by a digital-to-analog converter; wherein the output of the digital-to-analog converter is connected via an ohmic resistor to the negative input of a voltage amplifier, the output of which serves as the d-c voltage source and is connected to the measuring device; wherein the negative input of the voltage amplifier is additionally connected via an ohmic resistor to the voltage output of the measuring device and to ground; and wherein the positve input of the voltage amplifier is connected via an ohmic resistor to ground and another ohmic resistor to the output of the voltage amplifier.

* * * * *